United States Patent [19]

Toja et al.

[11] Patent Number: 4,897,414
[45] Date of Patent: Jan. 30, 1990

[54] DERIVATIVES OF 1-BENZENSULPHONYL-2-OXO-5-ALKYLTHIO PYRROLIDINE, AND COMPOSITIONS CONTAINING THEM

[75] Inventors: Emilio Toja, Milan; Carlo Zirotti, Arona; Fernando Barzaghi; Giulio Galliani, both of Monza, all of Italy

[73] Assignee: Roussel UCAF, Paris, France

[21] Appl. No.: 211,720

[22] Filed: Jun. 27, 1988

[30] Foreign Application Priority Data

Jun. 29, 1987 [IT] Italy .................. 21098 A/87

[51] Int. Cl.⁴ .................. C07D 207/48; A61K 31/40
[52] U.S. Cl. .................. 514/425; 548/542
[58] Field of Search .................. 548/542; 514/425

[56] References Cited

U.S. PATENT DOCUMENTS

| | | | |
|---|---|---|---|
| 3,117,975 | 1/1964 | Bortnick et al. | 548/545 |
| 3,423,426 | 1/1969 | Kohn | 548/542 |
| 3,686,169 | 8/1972 | Coran et al. | 548/542 |
| 4,585,769 | 4/1986 | Roger | 548/542 |

FOREIGN PATENT DOCUMENTS

| | | | |
|---|---|---|---|
| 0138721 | 4/1985 | European Pat. Off. | |
| 0224256 | 6/1987 | European Pat. Off. | 548/544 |
| 0229566 | 7/1987 | European Pat. Off. | 548/542 |

OTHER PUBLICATIONS

Drugs of the Future, vol. 10, No. 12, 1985, pp. 972, 974.

Primary Examiner—David B. Springer
Attorney, Agent, or Firm—Stevens, Davis, Miller & Mosher

[57] ABSTRACT

Compounds useful in the treatment of patients suffering from intellectual or nervous asthenias, memory failures, senescence or mental strain of the formula (I)

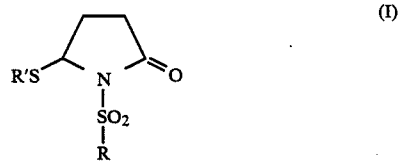

in which R' represents hydrogen, linear, branched or cyclic alkyl containing up to 8 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, possibly substituted, or a mono- or polycyclic heterocyclic aromatic radical possibly substituted; also process and intermediates for their preparation, therapeutic compositions containing those compounds and method of use.

6 Claims, No Drawings

DERIVATIVES OF 1-BENZENSULPHONYL-2-OXO-5-ALKYLTHIO PYRROLIDINE, AND COMPOSITIONS CONTAINING THEM

This invention relates to new derivatives of 1-benzenesulphonyl-2-oxo-5-alkylthio-pyrrolidine, the process and intermediates for their preparation, their use as medicaments and compositions containing them.

The subject of the invention is the compounds of general formula (I):

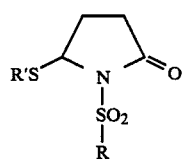

in which R' represents hydrogen, linear, branched or cyclic alkyl containing up to 8 carbon atoms, alkenyl containing from 2 to 8 carbon atoms, acyl containing from 1 to 6 carbon atoms or aralkyl containing from 7 to 15 carbon atoms and R represents aryl containing up to 14 carbon atoms, possibly substituted, or a mono- or polycyclic heterocyclic aromatic radical, possibly substituted.

As alkyl, there is preferred alkyl containing from 1 to 6 carbon atoms, for example, methyl, ethyl, n-propyl, isopropyl, n-butyl, isobutyl, tertbutyl, n-pentyl, n-hexyl, cyclopropyl, cyclobutyl, cyclopentyl or cyclohexyl.

As alkenyl, there is preferred ethenyl, propenyl or butenyl.

As acyl, there is preferred acetyl, propionyl or butyryl.

As aralkyl, there is preferred phenalkyl, particularly phenalkyl of 7 to 15 carbon atoms, e.g., benzyl or phenethyl.

As aryl, there is preferred phenyl or biphenylyl.

As heterocyclic radical, there is preferred furyl, thienyl, pyranyl, pyridyl, benzofuranyl, isobenzofuranyl, chromanyl, isochromanyl, chromenyl, xanthenyl, phenoxathienyl, oxazolyl, isoxazolyl, furazanyl, phenoxazinyl, thieno[2,3-b]furanyl, 2H-furo[3,2-b]pyranyl, benzoxazolyl or morpholinyl.

When R is substituted, it preferably carries as substituents one or more substituents chosen from the group constituted by free, esterified or etherified hydroxy in which the ester or ether part contains from 1 to 18 carbon atoms, such, for example, as acetoxy, methoxy or benzyloxy, the ketone and oxime functions, a linear, branched or cyclic, saturated or unsaturated, alkyl including up to 18 carbon atoms, for example, methyl, ethyl, propyl or isopropyl, ethenyl or ethynyl, halogen atoms such as fluorine, chlorine or bromine, a group $CF_3$, $SCF_3$, $OCF_3$, $NO_2$, $NH_2$ or $C\equiv N$, phenyl, acyl or alkoxycarbonyl groups containing from 2 to 8 carbon atoms and alkylsulphonyl group containing from 1 to 6 carbon atoms.

More particularly, the subject of the invention is the compounds of the formula (I) in which R represents an optionally substituted phenyl radical, as well as those in which R' represents a linear, branched or cyclic alkyl, containing up to 8 carbon atoms, such for example, as ethyl or isopropyl.

The invention has quite specially as its subject the compounds of which the preparation is given further on in the examples.

Among the preferred compounds of the invention, there can be cited the compounds of examples 1 and 3.

The compounds of the invention offer useful pharmacological properties; they retard the extinction of the conditioned avoidance response and they retard the disappearance of the learned response. They favour attention, vigilance and memorizing.

Therefore, a subject of the invention is the compounds of formula (I), as medicaments, useful in particular in the treatment of intellectual or nervous asthenias, memory failures, senescence, and mental fatigue.

The subject of the invention, as medicaments, is more particularly the products previously mentioned and notably the products of examples 1 and 3.

The usual daily dose is variable according to the affection concerned, the subject treated and the administration route; it can be between 0.6 mg and 40 mg/kg for example between 2 and 20 mg/kg in one or more doses for the product of example 1 administered by oral route.

The subject of the present invention is also the pharmaceutical compositions containing as active principle at least one compound of the formula (I).

The pharmaceutical compositions of the invention can be solid or liquid and are presented in the pharmaceutical forms currently used in human medicine, such as, for example, plain or sugar-coated tablets, capsules, granules, suppositories, and injectable preparations; they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

Also a subject of the invention is a process for the preparation of compounds of the formula (I), characterized in that a compound of the formula (II):

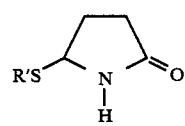

is submitted to the action of a compound with the formula (III):

in which Hal represents chlorine or bromine and R retains the same significance as previously indicated, in order to obtain the corresponding compound of the formula (I).

In a preferred method, the reaction between the compound of the formula (II) and the compound of the formula (III) is effectuated:

(a) in the presence of a strong base such as butyllithium, an alkali hydride such as sodium hydride, or sodium bis-(trimethylsilyl)amide;

(b) in a solvent chosen from the group constituted by tetrahydrofuran, benzene, dimethylformamide, dimethylsulphoxide or the diethyl ether of diethylene glycol.

The compounds of the formula (II) used as starting compounds can be prepared according to the following reactional scheme:

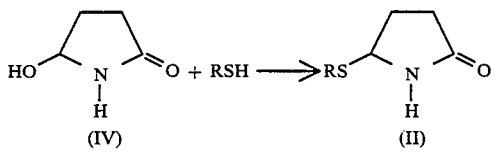

The compound (IV) is described in Heterocycles 22, (8), 1733 (1984).

The examples set out below describe the preparation of several compounds of formula (II).

These compounds of the formula (II) are new and are themselves one of the subjects of the present invention.

The following examples illustrate the invention without, however, limiting it.

EXAMPLE 1

1-benzenesulphonyl-2-oxo-5-ethylthio-pyrrolidine

To 3.1 g of 5-ethylthio pyrrolidin-2-one in 130 cm$^3$ of tetrahydrofuran there is added at −65° C., 14.2 cm$^3$ of a 1.6M solution of butyllithium in hexane. After 20 minutes, there is added 3.77 g of benzenesulphonyl chloride in 15 cm$^3$ of tetrahydrofuran. After allowing to return to ambient temperature and concentrating to dryness under reduced pressure, 4 g of the expected product is obtained. m.p. 100°–113° C., crystallized from ethanol.

| Analysis: | $C_{12}H_{15}NO_3S_2$. | | | | | |
|---|---|---|---|---|---|---|
| Calculated: | C % | 50.50 | H % | 5.30 | N % | 4.91 |
| Found: | | 50.23 | | 5.35 | | 4.94 |

PREPARATION 5-ethylthio-pyrrolidin-2-one

A mixture of 2.8 g of 5-hydroxy-pyrrolidin-2-one in 25 cm$^3$ of ethylmercaptan is made to react for 4 hours at 20° C. with 1.4 g of Amberlite IR 120 H. The mixture is diluted with ethyl ether, the solvent is distilled off, and 2.6 g of the expected product is obtained, m.p. 65°–68° C. after crystallizing from isopropyl ether, m.p. 68°–70° C.

| Analysis: | $C_6H_{11}NOS$. | | | | | |
|---|---|---|---|---|---|---|
| Calculated: | C % | 49.62 | H % | 7.63 | N % | 9.64 |
| Found: | | 49.85 | | 7.81 | | 9.83 |

EXAMPLE 2

1-(4-diphenyl)-sulphonyl-2-oxo-5-ethylthio-pyrrolidine

To 2.1 g of 5-ethylthio-pyrrolidin-2-one in solution in 155 cm$^3$ of tetrahydrofuran, there is added, at between −72° and −67° C., 9.6 cm$^3$ of a 1.6M solution of butyllithium in hexane. After 20 minutes at the same temperature, there is added 3.66 g of diphenylsulphonyl chloride in 20 cm$^3$ of tetrahydrofuran. After allowing to return to ambient temperature, concentrating and chromatographing on silica (eluent: toluene-ethyl acetate, 8-2), 1.7 g of the expected product is obtained. m.p. 125°–128° C., crystallized from isopropanol.

| Analysis: | $C_{18}H_{19}NO_3S_2$. | | | | | |
|---|---|---|---|---|---|---|
| Calculated: | C % | 59.81 | H % | 5.30 | N % | 3.87 |
| Found: | | 59.77 | | 5.28 | | 3.84 |

EXAMPLE 3

1-benzenesulphonyl-2-oxo-5-isopropylthio-pyrrolidine

To 2.5 g of 5-isopropylthio-pyrrolidin-2-one in 130 cm$^3$ of tetrahydrofuran, there is added at −70° to −65° C., 10.48 cm$^3$ of a 1.5M solution of butyllithium in hexane. This is maintained for 20 minutes at this temperature, then 2.76 g of benzenesulphonyl chloride is added in 25 cm$^3$ of tetrahydrofuran. After allowing to return to ambient temperature, concentrating under reduced pressure, taking up with water, filtering and drying, 2.15 g of the expected product is obtained. m.p., 91°–93° C., crystallized from ethanol.

| Analysis: | $C_{13}H_{17}NO_3S_2$. | | | | | |
|---|---|---|---|---|---|---|
| Calculated: | C % | 52.21 | H % | 5.72 | N % | 4.68 |
| Found: | | 51.86 | | 5.73 | | 4.62 |

PREPARATION 5-isopropylthio-pyrrolidin-2-one

A mixture of 9 g of 5-hydroxy-pyrrolidin-2-one in 40 cm$^3$ of 2-propanethiol and 5 g of Amberlite resin IR 120 H is maintained for 80 hours at ambient temperature. After diluting with ether, filtering, and concentrating under reduced pressure, 8.5 g of the expected product is obtained. m.p. 77°–79° C., crystallized from isopropyl ether. m.p. 85°–87° C. after re-crystallization.

| Analysis: | $C_7H_{13}NOS$ | | | | | |
|---|---|---|---|---|---|---|
| Calculated: | C % | 52.80 | H % | 8.23 | N % | 8.80 |
| Found: | | 52.56 | | 8.30 | | 8.81 |

EXAMPLE 4

1--(3--trifluoromethyl)-benzensulphonyl-2-oxo-5-isopropylthio-pyrrolidine

To 2.6 g of 5-isopropylthio-pyrrolidin-2-one in solution in 110 cm$^3$ of tetrahydrofuran, there is added at −70° C., 10.2 cm$^3$ of a 1.6M solution of butyllithium in hexane. After 20 minutes, 4 g of trifluoromethyl benzenesulphonyl chloride (J. Org. Chem. 25, 1824, (1960) is added in 20 cm$^3$ of tetrahyrofuran. After allowing to return to ambient temperature, concentrating, and washing with water, 3.15 g of the expected product is obtained. m.p. 105°–106° C., crystallized from ethanol.

| Analysis: | $C_{14}H_{16}F_3NO_3S_2$. | | | | | |
|---|---|---|---|---|---|---|
| Calculated: | C % | 45.77 | H % | 4.39 | N % | 3.81 |
| Found: | | 45.79 | | 4.36 | | 3.79 |

EXAMPLE 5

1-(4-nitrobenzene)sulphonyl-2-oxo-5-isopropylthio-pyrrolidine

To 2.9 g of 5-isopropylthio-pyrrolidin-2-one, in 120 cm³ of tetrahydrofuran, there is added at −70° C., 12.1 cm³ of a 1.5M solution of butyllithium in hexane. After 20 minutes, at −70° C., 4.03 g of 4-nitrobenzenesulphonyl chloride is added. After allowing to return to ambient temperature, concentrating and wasing with water, 3.2 g of the expected product is obtained. m.p. 125°–127° C., crystallized from ethanol.

| Analysis: | $C_{13}H_{16}NO_2O_5S_2$. | | | | | |
|---|---|---|---|---|---|---|
| Calculated: | C % | 45.33 | H % | 4.68 | N % | 8.13 |
| Found: | | 45.26 | | 4.67 | | 8.04. |

EXAMPLE 6

1-benzenesulphonyl-2-oxo-4-n-butylthio-pyrrolidine

To 3.1 g of 5-n-butylthio-pyrrolidin-2-one in 130 cm³ of tetrahydrofuran, there is added, at −65° C./−71° C., 11.2 cm³ of a 1.6M solution of butyllithium in hexane. After 20 minutes at the same temperature, 3.16 g of benzenesulphonyl chloride is added in 20 cm³ of tetrahydrofuran. After allowing to return to ambient temperature, concentrating to dryness, and chromatographing on silica (eluent: hexane-ethyl acetate, 1-1), 3.8 g of the expected product is obtained.

| Analysis: | $C_{14}H_{19}NO_3S_2$. | | | | | |
|---|---|---|---|---|---|---|
| Calculated: | C % | 53.65 | H % | 6.11 | N % | 4.47 |
| Found: | | 53.91 | | 6.17 | | 4.26 |

PREPARATION

5-n-butylthio-pyrrolidin-2-one

A mixture of 3.5 g of 5-hydroxy-pyrrolidin-2-one is agitated for 24 hours in 20 cm³ of 1-thiobutanol with 1.75 g of Amberlite 18 120 H resin. After distilling the solvent under reduced pressure, taking up with hexane, filtering, concentrating and chromatographing on silica (eluent: ethyl acetate), 4.5 g of the expected product is obtained. b.p. 230°–235° C., under 0.05 mbar.

| Analysis: | $C_8H_{15}NOS$ | | | | | |
|---|---|---|---|---|---|---|
| Calculated: | C % | 55.45 | H % | 8.72 | N % | 8.08 |
| Found: | | 55.28 | | 8.78 | | 8.05 |

EXAMPLE 7

1-benzenesulphonyl-2-oxo-5-propylthio-pyrrolidine

To 2.3 g of 5-propylthio-pyrrolidin-2-one in solution in 120 cm³ of tetrahydrofuran, there is added at −70° C./−65° C., 9.6 cm³ of a 1.5M solution of butyllithium in hexane. After 20 minutes at this temperature, 2.55 g of benzenesulphonyl chloride is added in 20 cm³ of tetrahydrofuran. After allowing to return slowly to ambient temperature, concentrating and chromatographing on silica (eluent: hexane-ethyl acetate, 3-7), 1.5 g of the expected product is obtained. m.p. 49°–51° C. crystallized from isopropyl ether.

| Analysis: | $C_{13}H_{17}NO_3S_2$. | | | | | |
|---|---|---|---|---|---|---|
| Calculated: | C % | 52.15 | H % | 5.72 | N % | 4.68 |
| Found: | | 52.37 | | 5.68 | | 4.77 |

PREPARATION

5-propylthio-pyrrolidin-2-one

A mixture of 4 g of 5-ethoxy-pyrrolidin-2-one, 30 cm³ of propanethiol and 2 g of Amberlite-15 resin is agitated for 2 hour 45 minutes at ambient temperature. The resin is filtered off, then the excess propanethiol is distillated. 2.8 g of the expected product is obtained, isolated from isopropyl ether. m.p. 40°–42° C.

| Analysis: | $C_7H_{13}NOS$ | | | | | |
|---|---|---|---|---|---|---|
| Calculated: | C % | 52.80 | H % | 8.23 | N % | 8.80 |
| Found: | | 52.86 | | 8.17 | | 8.81 |

EXAMPLE 8

1-(4-nitrobenzene)sulphonyl-2-oxo-5-ethylthio-pyrrolidine

To a solution of 2 g of 5-ethylthio-pyrrolidin-2-one in 110 cm³ of tetrahydrofuran, there is added at −70° C., 9.2 cm³ of a 1.5M solution of butyllithium in hexane. After 20 minutes at this temperature, 3.06 g of 4-nitro-benzene-sulphonyl chloride in solution in 10 cm³ of tetrahydrofuran is added. After allowing the temperature to rise slowly, concentrating to dryness, adding water, filtering and drying, 3 g of the expected product is obtained, m.p. 113°–115° C., crystallized from ethanol.

| Analysis: | $C_{12}H_{14}N_2O_5S_2$. | | | | | |
|---|---|---|---|---|---|---|
| Calculated: | C % | 43.62 | H % | 4.27 | N % | 8.48 |
| Found: | | 43.49 | | 4.24 | | 8.39 |

EXAMPLE 9

1-(3-fluoromethyl)benzensulphonyl-2-oxo-5-ethylthio-pyrrolidine

To a solution of 2 g of 5-ethylthio-pyrrolidin-2-one in 110 cm³ of tetrahydrofuran, there is added at −70° C., 9.2 cm³ of a 1.5M solution of butyllithium in hexane. After maintaining this for 20 minutes at this temperature, 3.36 g of 3-trifluoromethyl benzene-sulphonyl chloride is added. The temperature is allowed to return slowly to the ambient, and after concentrating to dryness, taking up with water, filtering and drying, 2.8 g of the expected product is obtained. m.p. 78°–79° C., crystallized from ethanol.

| Analysis: | $C_{13}H_{14}F_3NO_3S_2$. | | | | | |
|---|---|---|---|---|---|---|
| Calculated: | C % | 44.13 | H % | 3.99 | N % | 3.96 |
| Found: | | 44.11 | | 3.92 | | 3.87 |

EXAMPLE 10

1-(4-methoxy)benzenesulphonyl-2-oxo-5-ethylthio-pyrrolidine

To a solution of 1.85 g of 5-ethylthio-pyrrolidin-2-one in 100 cm$^3$ of tetrahydrofuran, there is added at −70° C., 8.5 cm$^3$ of a 1.5M solution of butyllithium in hexane. This temperature is maintained for 15 minutes, then 2.65 g of 4-methoxy benzenesulphonyl chloride is added in solution in tetrahydrofuran. After allowing to return to ambient temperature. concentrating to dryness, taking up with water, filtering and crystallizing twice from isopropanol, 2.2 g of the expected product is obtained. m.p. 95°–97° C.

| Analysis: | $C_{13}H_{17}NO_4S_2$. | | | | | |
|---|---|---|---|---|---|---|
| Calculated: | C % | 49.50 | H % | 5.43 | N % | 4.44 |
| Found | | 49.63 | | 5.38 | | 4.32 |

EXAMPLES OF PHARMACEUTICAL COMPOSITIONS (a) Tablets were prepared of the following formula:
Product of example 1: 100 mg
Excipient q.s. for a tablet finished at: 300 mg
(Detail of excipient: lactose, corn starch, treated starch rice, starch, magnesium stearate, talc).

(b) Capsules were prepared of the following formula:
Product of example 2: 200 mg
Excipient q.s. for a capsule finished at: 300 mg
(Detail of excipient: talc, magnesium stearate, aerosil).

PHARMACOLOGICAL STUDY

Acute toxicity and behaviour of the invention products

There were used male mice (Charles Rivers CD$_1$) weighing 22–23 g, without food for 16 hours. The products were administered to them by oral route at doses of 1000–500–250 mg/kg.

The effect of the products on the behaviour of the animals was evaluated according to the method described by Irvin (Psychopharmacologia (1968), 13, 222–257) during the first 8 hours and on the 24th hour.

The mortality was noted during the 7 days following the treatment.

The LD$_{50}$ was thus found to be greater than 1000 mg/kg products of examples 1 and 3.

Learning and memorizing

There were used male mice (Charles Rivers CD$_1$) weighing 25–30 g. The animals were placed in the luminous part of a box with two compartments communicating by an opening (G. Galliani, R. Cesana and F. Barzaghi, Med. Sci. Res. 15, 313–314, (1987)).

At the instant when the mouse passes from the luminous compartment to the dark compartment, the opening closes and it is immediately punished by an electric discharge to the paws. The animal submitted to this procedure learns to memorize the punishment. In fact, if it is put back in the luminous compartment, it will be thus avoid crossing the opening and re-entering the dark compartment.

In order to induce a retrograde amnesia, the animals are submitted immediately after learning to an electric shock. After the electric shock, the products are administered by oral route at doses of 12.5: 25; 50; 100; 200 and 400 mg/kg.

We used from 10 to 50 animals per dose.

The anti-amnesic effect of the products is evaluated 3 hour after the treatment, using the same procedure as that utilized for the acquisition.

The time taken by the animal to return to the dark chamber (time limit 180 seconds) is used as evaluation parameter.

In the same experimental conditions, the control animals enter with a time lapse of 40–50 seconds.

The active products are those which cause a significant increase in the latency time.

The results are expressed as percentages of the increase of the latency time in comparison with the corresponding controls. Results obtained with two reference products are provided.

The following Table shows the results:

TABLE

| Percentage increase in latency time in comparison with the controls | | | | | | |
|---|---|---|---|---|---|---|
| | Dose mg/kg per os | | | | | |
| Product of example | 400 | 200 | 100 | 50 | 25 | 12.5 |
| 1 | 98* | 151* | 101* | 71* | 50* | 9 |
| 2 | — | 100* | 105* | 45* | 32 | — |
| 3 | 105* | 110* | 79* | 66* | 18 | — |
| 4 | 106* | 77* | 71* | 46 | 21 | — |
| PIRACETAM | — | 20 | 48* | 10 | 19 | — |
| AMIRACETAM | — | 32 | 88* | 77* | 39 | — |

*Values statistically different in comparison with controls.

CONCLUSION

The products of the examples have shown an important antiamnesic effect at doses between 50 and 200 mg/kg per os and much greater than that of the reference products.

What is claimed is:

1. Compounds of the formula (I):

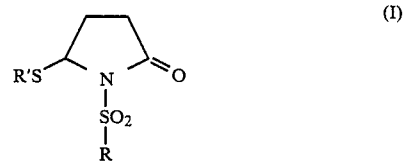

in which R' represents hydrogen, linear or branched alkyl containing up to 8 carbon atoms, alkenyl containing from 2 to 8 carbon atoms, or aralkyl containing from 7 to 15 carbon atoms and R represents phenyl possibly substituted by CF$_3$, NO$_2$, free esterified or etherified hydroxy in which the ester or ether part contains from 1 to 18 carbon atoms or phenyl.

2. Compounds of the formula (I) as defined in claim 1, in which R represents a possibly substituted phenyl.

3. Compounds of the formula (I) as defined in claim 1, in which R' represents a linear or, branched alkyl containing up to 8 carbon atoms.

4. Compounds of the formula (I) as defined in claim 3, in which R' represents ethyl or isopropyl.

5. A compound of the formula (I) as defined in claim 1, selected from the group consisting of 1-(benzenesulphonyl)-2-oxo-5-ethylthio-pyrrolidine and 1-(benzenesulphonyl)-2-oxo-5-isopropylthio-pyrrolidine.

6. A therapeutic composition, comprising a therapeutically effective amount of a compound as defined in any one of claims 1, 2, 3, 4 or 5, and a pharmaceutically acceable carrier.

* * * * *